United States Patent [19]

Likens, deceased et al.

[11] 4,229,437

[45] Oct. 21, 1980

[54] PASTE OR DOUGH-LIKE SALVE FOR TREATING SKIN

[75] Inventors: Jonas S. Likens, deceased, late of Lafayette, Tenn., by Ruby L. Ford, Jessie W. Likens, Mary F. L. Coulter, Pauline L. Coulter, heirs; Lucille L. Filson, heir, Rte. 1, Hartsville, Tenn. 37074

[73] Assignee: Lucille Likens Filson, Hartsville, Tenn.

[21] Appl. No.: 873,087

[22] Filed: Jul. 18, 1978

[51] Int. Cl.$^2$ ............... A61K 33/30; A61K 35/78
[52] U.S. Cl. ........................... 424/145; 424/195
[58] Field of Search ........................ 424/145, 195

[56] References Cited

U.S. PATENT DOCUMENTS

| | | | |
|---|---|---|---|
| 209,331 | 10/1878 | Daniel | 424/145 |
| 1,411,577 | 4/1922 | Mullins et al. | 424/145 |
| 2,344,830 | 3/1944 | Mohs | 424/145 |

OTHER PUBLICATIONS

Potter's Cyclopaedia of Botanical Drugs & Prep., Published by Potter & Clark, London (1950), p. 38.

*Primary Examiner*—Jerome D. Goldberg
*Attorney, Agent, or Firm*—Berman, Aisenberg & Platt

[57] ABSTRACT

Dried bittersweet root bark is combined with crystalline zinc chloride to form a salve which is topically applied to remove unwanted growths from the skin. The salve comprises an admixture of a major volumetric proportion of root bark with a minor volumetric proportion of zinc chloride crystals.

2 Claims, No Drawings

PASTE OR DOUGH-LIKE SALVE FOR TREATING SKIN

SUMMARY OF THE INVENTION

A composition which is a substantially uniform admixture of three parts by volume of bittersweet dried and ground root bark (BS) and one part by volume of zinc chloride (butter of zinc) crystals (BZ) is useful for removing an external surface lesion from the skin when the composition is applied in a thin layer directly on the lesion and secured there in an air-tight fashion for a period of time while keeping the lesion and surrounding area dry and warm. BS thus has an active component which, when compounded with zinc chloride, forms a medicament paste or salve useful for removing unwanted skin growths.

DETAILS

The plant referred to as bittersweet is also known as woody nightshade or *Solanum dulcamara*. The bark of the root of this plant is dried (e.g. until the bark is brittle) at a temperature from ambient temperature, e.g. about room temperature, i.e. 20° C., to about 250° F. (121° C.). When drying is effected at 250° F., drying for from about 45 to about 60 minutes (with occasional stirring) is ordinarily sufficient.

After drying the root bark until brittle, the dried bark is ground to a particle size (hereinafter referred to as powder) about the same as that of granulated sugar or even finer. The precise particle size is not critical.

Zinc chloride is a well-known compound which is available in crystalline form. Although the proportions are not exact, about one part by volume of zinc chloride crystals is compounded with three parts by volume of BS powder to formulate the subject composition. Compounding is effected, e.g., with a spatula on a suitable clean surface. The BS powder is mixed into the BZ to form a salve, paste or dough composition which is a substantially uniform admixture of the two components. These are the only essential ingredients; no other components are required for the composition or to achieve the desired results. The composition, however, is advantageously compounded immediately or shortly before use.

The composition is applied to an externally-visible unwanted skin growth or diseased area which is herein referred to as a lesion. This term is used to include those conditions variously known, e.g., as moles, stone moles, red moles and warts, which are removed by treatment with the composition. The existence, growth and/or spread of stone cancer (calcifying epithelioma), epithelioma adenoides cysticum or epithelioma capitis is also retarded or terminated by suitable treatment with the composition.

In order to treat a particular skin condition, a piece of clean cloth is cut to approximately the same size as the lesion. This piece of cloth is covered with the paste or dough composition (to a thickness of about that of a dime) to form a plaster with which the lesion is covered. The composition is placed directly on the lesion, and the plaster is secured in place with, e.g., adhesive tape in an air-tight manner. For twenty-four hours thereafter (for a lesion the size of a pea or smaller) the area of the lesion is kept dry and warm. Body temperature is more than adequate; the lesion area should not be permitted to contact anything having a temperature below about 15° C. (60° F.) during the specified period. (Larger lesions will require at least forty-eight hours or even longer.)

Pain is experienced for eleven or twelve hours, and it is accompanied by redness and swelling of the involved area. At the end of the twenty-four-hour (or longer) period, the plaster is removed. The entire area is thereafter bathed twice or three times daily with luke-warm water and mild soap and then dried. Between washings the lesion and surrounding area are covered with petroleum jelly or other suitable ointment or emollient, over which a thin cloth is maintained, preferably without any type. This is continued (usually for about seven days) until the lesion is removed.

At the end of the initial application of the composition, the plaster is raised and the lesion is examined. If the treated area looks white around the edges and the lesion appears to be breaking loose, the composition has been applied for a sufficient period; otherwise, apply another similar plaster for a further twenty-four hours and maintain it under the same conditions during this period. During treatment with the composition the center of the leasion may turn black.

The following examples are merely illustrative and in no way limitative of the subject invention. In the examples all parts are by volume and all temperatures are in degrees celsius unless otherwise stated.

EXAMPLE 1

Heat an oven to a temperature of 121° and place therein the bark of the roots of *solanum dulcmara*. Fifty minutes thereafter check the bark. On finding the bark dry and brittle, remove the bark from the oven and grind the bark to a powder having a particle size about that of granulated sugar or finer.

With a spatula and on a smooth stone (or other) surface mix three parts of ground bark (BS) with one part of zinc chloride crystals (BZ) until a substantially uniform admixture is obtained in the form of a salve or paste.

EXAMPLE 2

A 39 year old male (MC) was diagnosed by a practicing and qualified physician as having a lesion on the left side of his forehead. Under the observation of the physician a piece of clean white cloth, the size of the lesion, was covered (to the thickness of about that of a dime) with freshly-prepared salve or paste (compounded according to Example 1) to form a plaster. The plaster was placed over the lesion so that the salve was in direct contact with and completely covered the lesion. The plaster was then secured in place with adhesive tape in an air-tight manner, where it was maintained undisturbed and out of contact with moisture for a period of 48 hours.

At the end of that time the tape was removed and the plaster was raised to observe the condition of the lesion, which had a blackish center and appeared white around the edges. The area about the lesion and a considerable surrounding portion of the subject's face was puffed up (swollen).

The plaster was completely removed; the lesion was bathed in luke-warm water with mild soap and then dried. The lesion was then covered with vaseline on which a clean soft white cloth was gently placed and maintained. The washing and drying were repeated twice daily; covering with vaseline was effected after each drying and one additional time each day for seven days, after which a growth (previously referred to as a lesion) fell out. Thereafter the washing and drying were discontinued, but the vaseline treatment (three times each day) was continued until the area was healed.

EXAMPLE 3

The growth removed from MC's forehead in Example 2 was submitted by the physician to a hospital for a pathological report. The report, signed by a qualified pathologist, stated that the "specimen consists of an irregular fragment of ragged, gray-white material measuring 2.0×1.5×0.4 cm. The specimen is serially sectioned and representative sections are submitted. (rwk:cb)"

Microscopic: "Multiple sections show skin with a markedly thin epidermis. In the underlying dermis are nests and sheets of basal cell carcinoma, some of which are surrounded at the periphery by palisading hyperchromatic cells. Marked degeneration and autolysis are noted at the margins of reaction. The deep margin is involved with tumor."

Diagnosis: "Skin ellipse, head—basal cell carcinoma. Deep margin involved with tumor; lateral margins indeterminate. (1)"

EXAMPLE 4

Four months after the treatment referred to in Example 2, a biopsy was made of the area of MC's forehead from which the growth had been removed. At that time there was a small unhealed center in the scar, and an ellipseal incision was made widely around the sinus area. This was sent to the same hospital for a pathological report, which was rendered by the same pathologist. The report states that the "specimen consists of an ellipse measuring 1.4×0.6×0.5 cm. The epidermal surface has a slight gray lesion measuring 0.2 cm. in diameter. On cut surface the dermis is gray-white and thickened. Representative sections are submitted. (rwk:cb)"

Microscopic: "These sections of skin show an intact elevated epidermis. In the dermis is a nodule consisting of dense collagen. The collagen is arranged in an irregularly intertwining fashion. Around the nodule is a scanty lymphocytic infiltrate. There is no evidence of atypia or malignancy."

Diagnosis: "Nodular subepidermal fibrosis in biopsy from forehead, no malignancy. (1)"

EXAMPLE 5

To treat a melanocytic nevus above and to the right of the chin of a 40 year old white male, a piece of clean white cloth (just slightly larger than the nevus) is covered (to a fairly uniform thickness approximating that of a dime) with freshly-prepared salve or paste compounded according to Example 1, thus forming a plaster. The nevus and surrounding area are dried, and the plaster is placed over the nevus so that the salve or paste is in direct contact with the nevus. The plaster is then secured in place with adhesive tape in a manner designed to exclude external air from the nevus.

For a period of twenty-four hours the adhesive tape and the involved skin area are kept dry and are maintained out of contact of anything having a temperature below about 20°. Thereafter the adhesive is lifted to observe the condition of the nevus, which appears to be circumscribed by a whitish perimeter.

The nevus and immediately surrounding skin is then washed with luke warm water and mild soap and dried before covering it with petroleum jelly. Soft white cloth or gauze is placed over the nevus and maintained in place by contact with the petroleum jelly. Petroleum jelly is kept on the nevus in this manner between washings (and dryings), which are effected twice daily. After eight days the nevus separates from the skin and is effectively removed. Bathing the involved skin and keeping the clean and dried skin in contact with petroleum jelly is continued until the area is healed.

The invention and its advantages are readily understood from the foregoing description. Although it is apparent that various changes may be made in the process and compositions without departing from the spirit or scope of the invention or sacrificing its material advantages, the composition requires a combination of the two ingredients indicated to be essential. Neither ingredient alone will produce the results obtained with the combination. The hereinbefore described processes and products are merely illustrative of preferred embodiments of the invention.

What is claimed is:

1. A paste or dough-like salve for treating skin topically which is substantially hemogeneous and consists essentially of an admixture of a minor volumetric effective proportion of zinc chloride crystals with a major volumetric effective proportion of dried and ground bark of roots from *Solanum dulcamara*.

2. An admixture according to claim 1 wherein the volumetric proportion of bark to zinc chloride crystals is approximately 3 to 1.

* * * * *